United States Patent [19]

Nolan et al.

[11] 4,213,458
[45] Jul. 22, 1980

[54] SEALING AND ATTACHMENT ASSEMBLY FOR MEDICAL DRAINAGE POUCH

[75] Inventors: John L. Nolan, Glenview; Harvey M. Nordby, Buffalo Grove, both of Ill.

[73] Assignee: Hollister Incorporated, Chicago, Ill.

[21] Appl. No.: 906,401

[22] Filed: May 17, 1978

Related U.S. Application Data

[63] Continuation-in-part of Ser. No. 783,340, Mar. 31, 1977, abandoned.

[51] Int. Cl.$^2$ .............................................. A61F 5/44
[52] U.S. Cl. ................................................... 128/283
[58] Field of Search ................................ 128/283, 295

[56] References Cited

U.S. PATENT DOCUMENTS

| | | | |
|---|---|---|---|
| 3,039,464 | 6/1962 | Galindo | 128/283 |
| 3,351,061 | 11/1967 | Nolan | 128/283 |
| 3,618,606 | 11/1971 | Brown et al. | 128/283 |
| 3,822,704 | 7/1974 | Nolan | 128/2 83 |
| 3,897,780 | 8/1975 | Trousil | 128/295 |
| 3,897,781 | 8/1975 | Marsan | 128/283 |
| 3,902,496 | 9/1975 | Eakin | 128/283 |
| 3,954,105 | 5/1976 | Nordby et al. | 128/283 |

FOREIGN PATENT DOCUMENTS 2110361  9/1971  Fed. Rep. of Germany ........... 128/283
1470419  4/1977  United Kingdom .

*Primary Examiner*—Robert W. Michell
*Assistant Examiner*—C. F. Rosenbaum

[57] ABSTRACT

A medical drainage pouch is provided with a breathable microporous adhesive patch for attaching the pouch to the body of a patient. The pouch includes a moisture-impermeable plastic bag having a drainage opening. A plastic annular retainer ring may be secured to the bag around the drainage opening. The adhesive patch has a thin non-woven porous backing sheet which is relatively easy to tear, and the patch is attached to the bag by a flexible annular attaching ring. The attaching ring may comprise a first layer of plastic and a second layer of hot melt adhesive. The plastic layer of the attaching ring is heat-sealed to the retainer ring or to the bag around a generally circular area of attachment, and the adhesive patch is heat-sealed to the adhesive layer of the attaching ring around a generally circular area of attachment which extends radially outwardly beyond the first area of attachment. The outward extension of the attaching ring provides a flexible, shock-absorbing connection between the tearable adhesive patch and the retainer ring or bag, and forces which are exerted on the adhesive patch, e.g., by the weight of the bag, are directed linearly with respect to the adhesive patch so that the tendency of the patch to tear is minimized.

25 Claims, 14 Drawing Figures

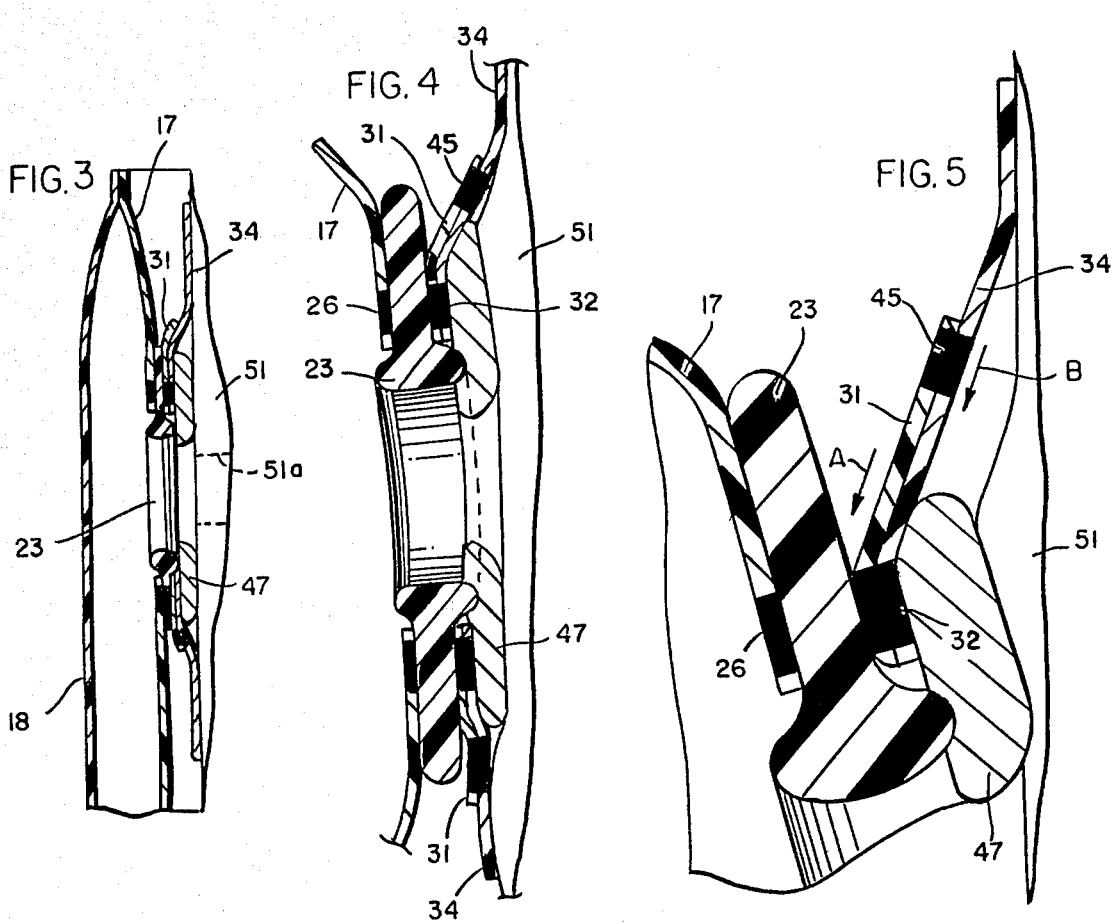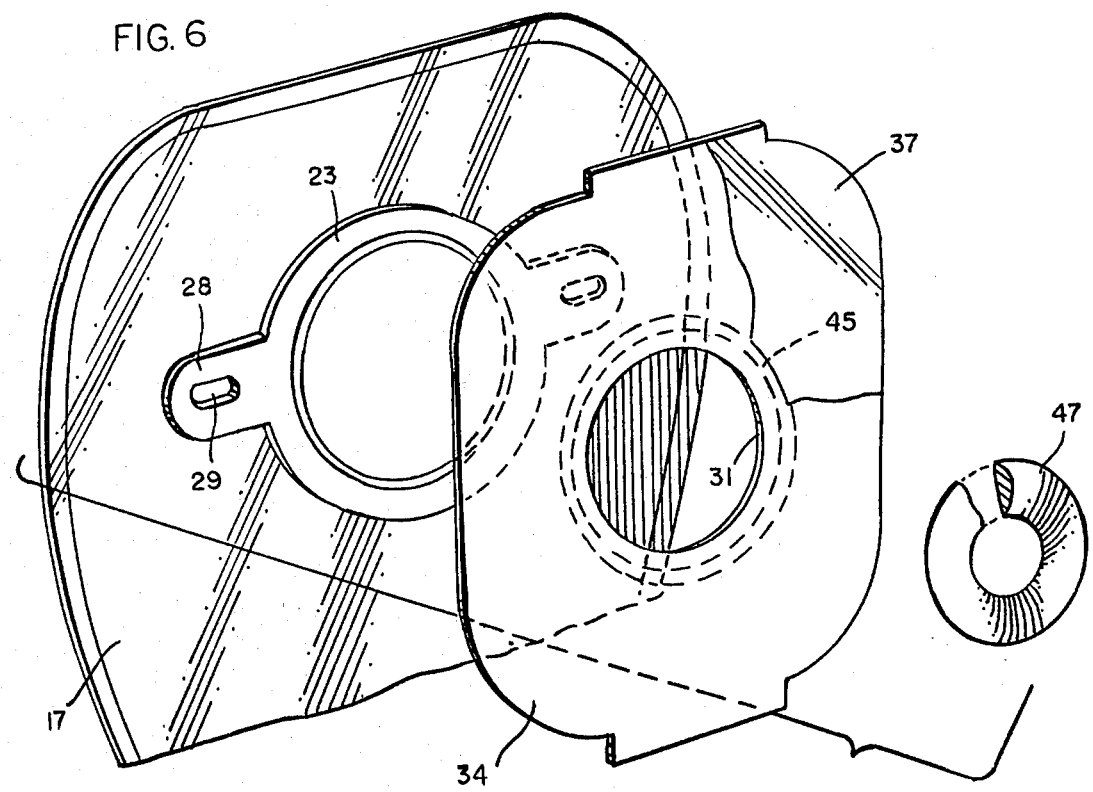

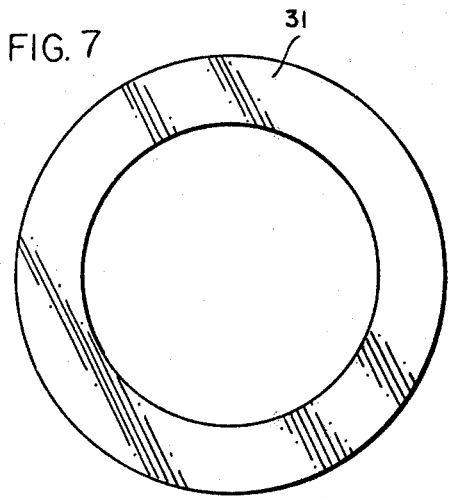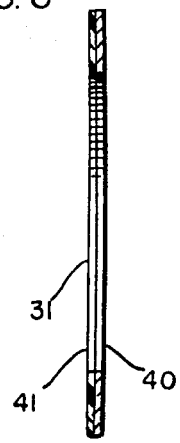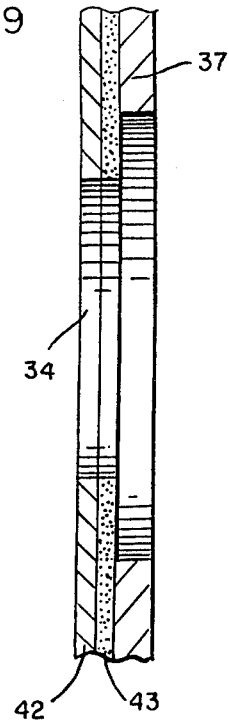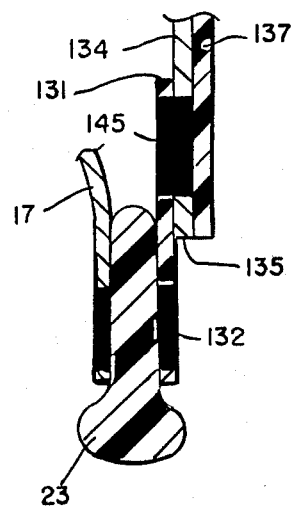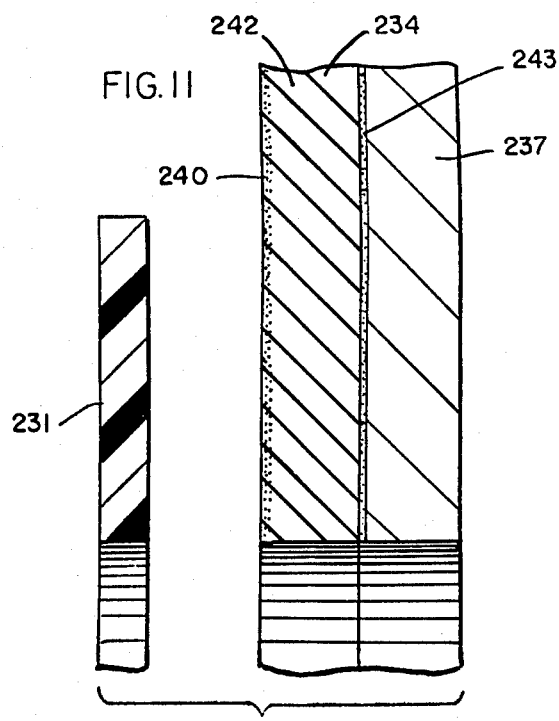

SEALING AND ATTACHMENT ASSEMBLY FOR MEDICAL DRAINAGE POUCH

CROSS-REFERENCE

This application is a continuation-in-part of co-pending application Ser. No. 783,340, filed March 31, 1977 and now abandoned.

BACKGROUND OF THE INVENTION

This invention relates to medical drainage pouches, and, more particularly, to an improved sealing assembly for such drainage pouches, which include surgical pouches for stoma or wound drainage, fecal collectors, enema bags, urostomy bags, etc.

Certain surgery, such as abdominal surgery known as colostomy, ileostomy, ureterostomy and the like, results in an opening, for example, in the abdominal wall, which permits drainage from the interior of a body cavity. The patient cannot control the drainage, and therefore a surgical drainage appliance in the form of a pouch or bag is used to contain the drainage.

U.S. Pat. Nos. 3,302,647 and 3,822,704 disclose prior art surgical drainage pouches, as used particularly for stoma or wound drainage. Each of these pouches includes a plastic bag for containing the fluid which is drained from the body and a relatively rigid plastic retainer ring which is heatsealed to the bag around the drainage opening in the bag. The drainage pouch described in U.S. Pat. No. 3,302,647 includes a sealing pad or ring formed from a mixture of karaya powder and glycerol. The drainage pouch described in U.S. Pat. No. 3,822,704 includes an adhesive patch which is secured to the relatively rigid retaining ring. A release paper covers the adhesive surface of the adhesive patch, and when the release paper is removed, the adhesive patch can be adhesively secured to the patient's body.

Current commercial surgical drainage pouches are similar to the pouch described in U.S. Pat. No. 3,822,704. The adhesive patch is formed from a nonporous surgical adhesive tape. This tape may comprise a backing sheet of nonporous polyethylene coated with a layer of pressure-sensitive adhesive. The relatively rigid retainer ring can be formed of polyethylene, and the adhesive patch secured to the retainer ring by heat-sealing the polyethylene backing of the adhesive patch to the polyethylene retainer ring. Alternatively, the nonporous adhesive patch can be heat-sealed directly to the pouch around the opening.

Drainage pouches which are provided with such a nonporous polyethylene adhesive patch are sold with and without a karaya sealing ring of the type described in U.S. Pat. No. 3,302,647. The adhesive patch is much larger than the karaya sealing ring, which is intended to seal the area adjacent the stoma against irritating fluids. The adhesive patch is adhesively secured to the body radially outwardly of the karaya ring to provide additional mechanical securement.

While such nonporous adhesive patches provide good adhesive and mechanical securement, certain problems have arisen. Since polyethylene or similar patches are not porous, the skin cannot breathe through the patch. The patch traps moisture against the skin and might cause an increase in the skin irritation of the patient.

Porous non-woven surgical adhesive tape is available. For example, a porous non-woven surgical tape is available under the brand name "Micropore" from Minnesota Mining & Manufacturing Company, of Minneapolis, Minn. This tape is formed from a backing layer of porous, non-woven rayon fabric and a layer of hypoallergenic, synthetic, acrylic pressure-sensitive adhesive. Such tape is essentially continuous in appearance and is non-perforated but exhibits a porosity which permits the skin to breathe through the tape. Because the pores of the tape are quite small and the tape appears to be essentially continuous, the tape is considered microporous.

Our attempts to substitute a porous non-woven surgical adhesive tape for the polyethylene adhesive patch on the drainage pouch were initially unsuccessful. First of all, the non-woven fabric backing layer of the tape cannot be satisfactorily heatsealed directly to the plastic retainer ring or to the pouch. We found that some other means of attaching the fabric backing to the retainer ring must be used. We also found that the very thin non-woven fabric is very easily torn at any concentrated stress point. For example, the fabric is easily tearable when it is subjected to a force tending to peel it away from an area of attachment or when it is subjected to a force which is directed angularly with respect to the plane of the fabric. Since the drainage pouch fills with fluid and becomes quite heavy, the force which tends to peel the retainer ring away from the adhesive patch which secures the pouch to the skin can become substantial and tear the patch causing leakage.

SUMMARY OF THE INVENTION

We have been able to overcome the problems of using non-woven porous fabric with drainage pouches by attaching the fabric to the retainer ring of the pouch with a flexible attaching ring. The flexible attaching ring is made from a material, for example, polyethylene, which can be easily heat-sealed to the retainer ring or to the pouch. The porous non-woven fabric is attached to the flexible attaching ring or bag in a circular area extending radially outwardly of the heat-sealed area between the attaching ring and the retainer ring or the bag. The attachment between the microporous backing sheet and the attaching ring can be made by heat-sealable adhesive, which is applied either to the attaching ring, or to the backing sheet, or both. For example, a hot melt adhesive can be used on the attaching ring which when melted flows into the pores of the fabric and provides a good adhesive and mechanical bond between the attaching ring and the microporous sheet. A force which tends to peel the retainer ring of the pouch away from the microporous adhesive patch is resisted by the heat seal attachment between the flexible plastic attaching ring and the plastic retainer ring or bag, and the heat seal bond between these parts is extremely strong and will resist normal tearing forces. Since the attaching ring is flexible, the attaching ring and the fabric will extend linearly or in a plane in the area of the bond between the attaching ring and the fabric. The force tending to separate the attaching ring and the adhesive patch is essentially a shear force which is aligned with the planes of the attaching ring and the patch in the area of the bond, and even though the microporous backing is easy to tear, it has sufficient strength to resist such linearly directed forces of the magnitude which would normally be encountered. We have found that microporous patches provide better adhesion to the skin than nonporous polyethylene tape since the breathable patches do not trap moisture between the patch and the skin. Further, the attaching ring may be utilized as a moisture barrier around the bag opening when no retainer ring is employed.

DESCRIPTION OF THE DRAWING

The invention will be explained in conjunction with illustrative embodiments shown in the accompanying drawing, in which:

FIG. 3 is a fragmentary sectional view showing the pouch secured to the body of a patient;

FIG. 4 is an enlarged fragmentary sectional view showing a force applied to the adhesive patch tending to pull the patch away from the skin;

FIG. 5 is an enlarged view of a portion of FIG. 4;

FIG. 6 is an exploded fragmentary perspective view of the drainage pouch;

FIG. 7 is a plan view of the flexible attaching ring;

FIG. 8 is a sectional view taken along the line 8—8 of FIG. 7;

FIG. 9 is a sectional view of the adhesive patch;

FIG. 10 is a fragmentary sectional view similar to FIG. 2 showing a modified embodiment of the sealing assembly;

FIG. 11 is a fragmentary sectional view showing a modified method of bonding the adhesive patch to the flexible attaching ring;

GENERAL DESCRIPTION

The invention relates to a sealing and attachment assembly for a drainage pouch having a moisture-impermeable bag formed of thermoplastic sheet material with the drainage opening in one side thereof and including an adhesive patch formed of microporous sheet material with an opening therein generally concentric with the bag opening. The outer side of the adhesive patch is coated with the pressure-sensitive adhesive for attachment to the body of a wearer and the inner side is connected to the bag. The improvement comprises means for connecting the microporous patch to the bag including an annular attaching ring formed of nonporous flexible plastic sheet material. The ring is positioned adjacent the patch inner side and arranged concentrically with respect to the bag and patch openings. At least the opposed annular outer portion of the ring is adhesively attached to the patch inner side. The annular inner portion of the other side of the ring provides a heat-sealed connection to the bag, either directly or through a retaining ring which in turn is heat-sealed to the bag. The annular outer portion of the inside of the attaching ring is unconnected and free to flex with the patch.

DESCRIPTION OF PREFERRED EMBODIMENTS

Figures 1, 2:
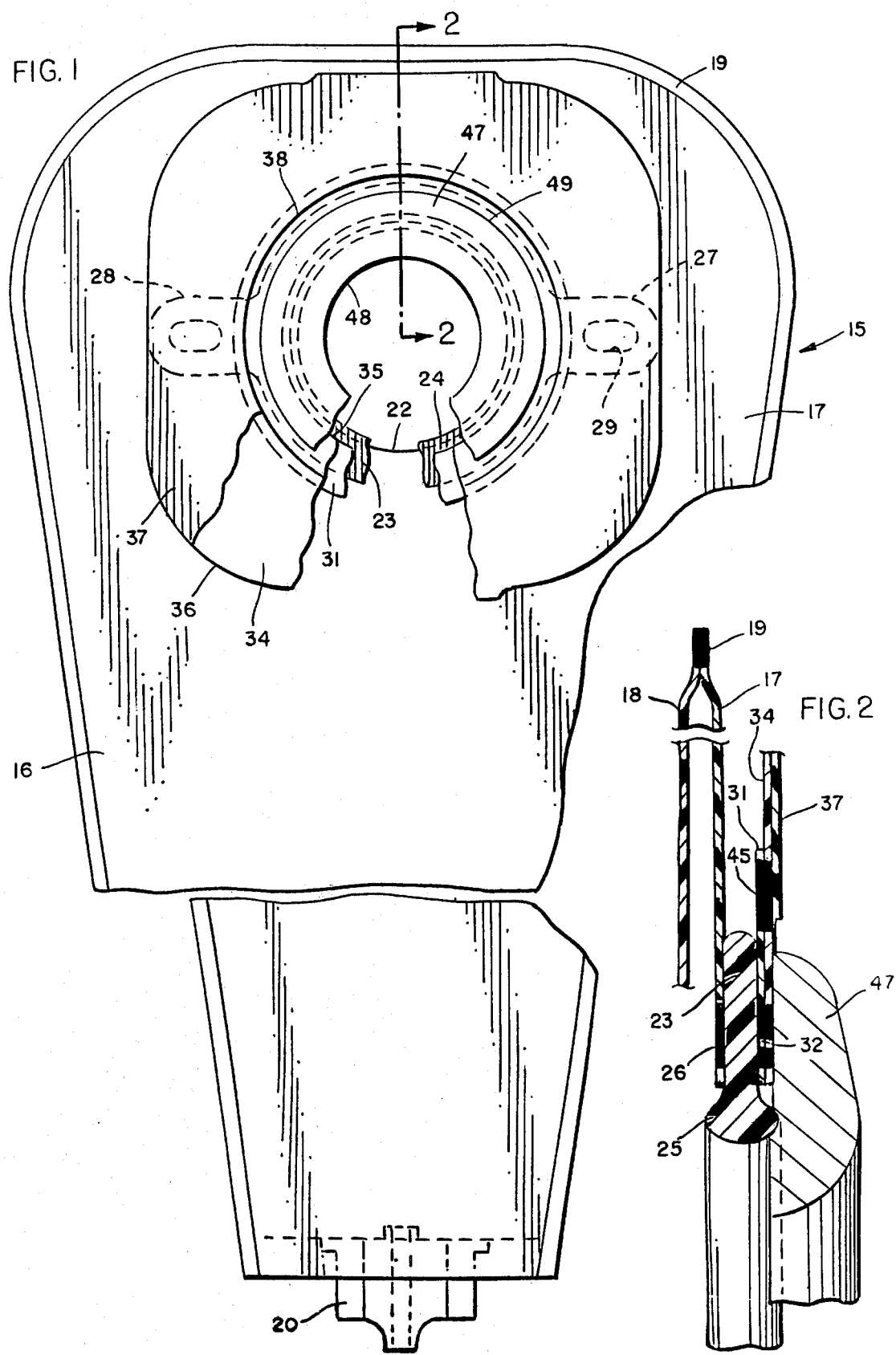
FIG. 1 is an elevational view, partially broken away, of a drainage pouch equipped with a sealing assembly formed in accordance with the invention.
FIG. 2 is a sectional view taken along the line 2—2 of FIG. 1.

Referring first to FIGS. 1 and 2, the numeral 15 designates generally a drainage pouch of the type described in U.S. Pat. Nos. 3,302,647 and 3,822,704. The pouch includes a bag 16 which is formed from a pair of moisture-impermeable thermoplastic films 17 and 18, such as polyethylene film, which are heat-sealed together around the periphery 19 thereof. The bottom of the bag may be provided with a drainage valve 20, if desired.

The plastic film 17 is provided with a circular drainage opening 22 in the upper portion thereof, and a thermoplastic retainer ring or gasket 23 is secured to the plastic film around the opening 22. The retainer ring is provided with a central opening 24 which is defined by an axially enlarged flange 25 (FIG. 2), and the retainer ring is secured to the plastic film 17 by heat-sealing the film and the retainer ring in an annularly shaped area around the drainage opening of the bag indicated at 26 in FIG. 2. The retainer ring is advantageously formed of polyethylene so that it can be easily heat-sealed to the polyethylene plastic film of the bag.

Referring again to FIG. 1, the retainer ring includes a pair of radially outwardly extending wings 27 and 28, each of which is provided with a slotted opening 29 which permits the retainer ring to be attached to the conventional belt which surrounds the patient and helps support the drainage pouch. The retainer ring is relatively thick and rigid and is capable of retaining its shape under the stress imposed by the belt.

A flexible plastic annular attaching ring 31 is secured to the retainer ring 23 on the side of the retainer ring opposite the plastic bag. Preferably, ring 31 or the inner layer thereof is formed of a thermoplastic film having a thickness of not over 10 mils, such as 2–5 mils, thereby being highly flexible. In the particular embodiment illustrated the flexible attaching ring has inside and outside diameters which are slightly greater than the inside and outside diameters, respectively, of the retainer ring 23 so that an annular outer portion of the attaching ring extends radially outwardly beyond the periphery of the retainer ring (except in the area of the wings 27 and 28). The attaching ring 31 is heat-sealed to the retainer ring 23 by a generally annularly shaped heat sealed area indicated at 32 in FIG. 2 which is adjacent the inner periphery of the attaching ring and which generally overlies the heat seal attachment 26 between the retainer ring and the plastic bag.

A generally rectilinear patch 34 of porous adhesive tape is secured to the annular attaching ring 31 on the surface of the ring opposite the surface which is bonded to the retainer ring 23. The adhesive patch is provided with an opening 35 having a diameter substantially the same as the inner diameter of the annular attaching ring, and the adhesive patch extends substantially outwardly of the attaching ring and retainer ring and terminates in a generally rectilinear periphery 36.

The porous adhesive patch is advantageously formed of non-woven microporous sheet material such as rayon, paper, etc., coated with a surgical pressure-sensitive adhesive. For example non-woven rayon fabric can be used. Such porous non-woven fabric, is available from Minnesota Mining & Manufacturing Company (3M) of Minneapolis, Minn. It is sold in roll form under the brand name "Micropore" by 3M. Similar microporous tape is available from other manufacturers, such as Johnson & Johnson under the brand name "Permacel".

Both of these adhesive tapes are porous and breathable but are capable of being torn quite easily. One particular "Micropore" tape which has been used has a thickness of 0.0045±0.0015 inch. While this tape had a specified tensile breaking strength of at least 5 pounds per inch, the tape could be torn by a force substantially less than 5 pounds.

More specifically, the adhesive tape for the patch may consist of a backing layer of porous non-woven rayon fabric and an adhesive layer of hypo-allergenic, synthetic, acrylic pressuresensitive adhesive. The pressure-sensitive adhesive can be covered by a silicone-coated release paper 37 which has a central opening 38.

In order to provide a good bond between the annular attaching ring 31 and the fabric layer of the adhesive patch 34, the attaching ring can be provided with a layer 40 (FIG. 8) of hot melt adhesive which is extrusion coated to a polyethylene layer 41. Since the adhesive layer is extrusion coated to the polyethylene layer a satisfactory bond is obtained. The polyethylene layer of the attaching ring is easily heat-sealed or fused to the polyethylene retainer ring 23, and when the hot melt adhesive layer of the attaching ring is pressed against the fabric layer of the adhesive patch under heat, the hot melt adhesive will flow into the pores of the fabric and provide a good mechanical and adhesive bond between the attaching ring and the adhesive patch. One particular type of hot melt adhesive that has been used is an ethyl vinyl acetate copolymer adhesive. In one embodiment of the annular attaching ring, the polyethylene layer 41 was 0.003 inch thick and the adhesive layer 40 was also 0.003 inch thick.

An enlarged sectional view of the adhesive patch 34 is shown in FIG. 9. The patch includes a layer 42 of non-woven fabric which is bonded to the adhesive layer 40 of the attaching ring, a layer 43 of pressure-sensitive adhesive which is intended to be applied to the skin of the patient, and the liner 37 of silicone-coated release paper.

Referring again to FIG. 2, the fabric layer of the adhesive patch 34 is bonded to the adhesive-coated attaching ring 31 in an annular shaped heat-seal area designated 45 which is spaced radially outwardly of the heat seal 32 between the attaching ring and the retainer ring 23. In one specific embodiment of the invention the width of both of the annularly shaped heat seal zones 32 and 45, i.e., the distance between the inner and outer diameters of the heat seal zones, was ⅛ inch, and the distance between the outer diameter of the inner heat seal zone 32 and the inner diameter of the outer heat seal zone 45 on the attaching ring was about 5/32 inch. The heat seal areas 32 and/or 45 can be made wider or made to overlap providing the area 45 extends outwardly a substantial distance beyond area 32.

The particular drainage pouch illustrated in FIGS. 1 and 2 includes an annular adhesive sealing pad or ring 47. The sealing pad is formed from a mixture of karaya and glycerol as described in U.S. Pat. No. 3,302,647 and is intended to provide a seal around the drainage opening in the body to protect the skin. The sealing pad 47 is provided with a central opening 48 which is concentric with the openings in the retainer ring 23, attaching ring 31, and adhesive patch 34, and the circular outer periphery 49 of the sealing pad has a diameter smaller than the diameter of the opening 38 in the release paper 37. The sealing pad 47 is secured to the adhesive patch by the adhesive property of the sealing pad and the adhesive layer of the adhesive patch.

FIG. 3 illustrates the drainage pouch secured to the skin 51 of a patient around a drainage opening. The release paper 37 is first removed from the adhesive surface of the adhesive patch 34, and the Karaya sealing pad 47 is pressed against the skin around the drainage opening called the stoma. The Karaya pad is deformable and will be flattened somewhat as it is pressed against the skin. The adhesive patch is then pressed against the skin outwardly of the Karaya pad and adhesively secured thereto. The drainage pouch can be further supported by attachment of the conventional belt to the attaching wings 27 and 28 of the retainer ring 23.

FIGS. 4 and 5 illustrate the drainage pouch and sealing assembly when a force tending to pull the adhesive patch away from the skin is applied to the pouch, e.g., by the weight of fluid contained by the plastic bag. The upper portion of the retainer ring 23 tends to pivot about the lower edge thereof, and the adhesive patch 34 is subjected to a force tending to pull the patch away from the skin. However, because both the annular attaching ring 31 and the adhesive patch 34 are flexible, the pulling force A exerted by the retainer ring 23 on the attaching ring 31 and the adhesive patch 34 tends to straighten the attaching ring and the adhesive patch along a line extending between the attachment of the attaching ring to the retainer ring and the attachment of the adhesive patch to the skin as shown in FIG. 5. Accordingly, the force B exerted on the adhesive patch in the area of the heat seal bond 45 is essentially linearly directed, i.e., the force vector lies substantially in the plane of the adhesive patch. Although the adhesive patch can be torn easily, the adhesive patch is sufficiently strong to resist linearly directed forces of the magnitude which would ordinarily be encountered during use of the pouch. The portion of the adhesive patch adjacent the skin curves smoothly into contact with the skin because the skin will be pulled outwardly somewhat, and concentrated stress areas which could tear the patch are thereby avoided in that area.

The force indicated by the arrow A tends to peel the attaching ring away from the retainer ring and is resisted by the heat seal bond 32 between the attaching ring and the retainer ring. Since the heat seal bond between the polyethylene layer of the attaching ring and the polyethylene retainer ring is a fusion bond, the bond is extremely strong and is easily capable of resisting this peeling force.

In the embodiment illustrated in FIGS. 1–4, the diameter of the opening in the adhesive patch is substantially the same as the inside diameter of the annular attaching ring 31. Accordingly, the adhesive patch extends radially inwardly beyond the outer heat seal bond 45 and is also bonded to the adhesive layer of the attaching ring in the heat seal zone 32. However, this inner attachment between the adhesive patch and the attaching ring is not required to withstand any peeling forces since the force tending to separate the adhesive patch and the attaching ring is taken up by the outer heat seal zone 45.

FIG. 6 illustrates the manner in which the drainage pouch is assembled. The attaching ring 31 is first bonded to the adhesive patch 34, which is covered with the release paper 37, by the outer annular heat seal ring 45. Thereafter, the attaching ring and adhesive patch is placed over the retainer ring 23 which has already been heat sealed to the plastic film 17. The attaching ring is then heat sealed to the retainer ring by the inner heat seal ring 32 (FIG. 2), which also bonds the adhesive patch to the attaching ring. The Karaya sealing pad 47 is then secured to the portion of the adhesive patch which is exposed by the opening in the release paper 37.

If desired, the drainage pouch can be sold without a Karaya sealing pad 47, and the user can apply a Karaya sealing pad or an equivalent sealing means himself before using the drainage pouch. If the drainage pouch is sold without a Karaya sealing pad, the central opening in the release paper is reduced so that the release paper covers the entire adhesive surface of the adhesive patch. For applications other than stoma drainage, the Karaya ring is frequently omitted.

FIG. 10 illustrates a modified embodiment in which the diameter of the central opening 135 of the adhesive patch 134 is greater than the diameter of the inner heat sealing ring 132. The adhesive patch is therefore heat-sealed to the attaching ring 132 only in the area of the outer heat seal ring 145. The adhesive surface of the adhesive patch is protected by the release paper 137.

The embodiment shown in FIG. 10 will function in the same way as the embodiment shown in FIG. 5. A force which tends to pull the adhesive patch away from the skin will cause the flexible attaching ring to extend in a substantially straight line between the inner heat seal ring 132 and the area of attachment between the adhesive patch and the skin, and the force tending to pull the adhesive patch and the attaching ring apart will be substantially linearly directed.

FIG. 11 illustrates an alternate method of attaching the adhesive patch to the sealing ring. The attaching ring 231 is formed from a single layer of polyethylene, and layer 240 of breathable heat-sealable adhesive is impregnated into the non-woven fabric layer 242 of the adhesive patch 234. The adhesive patch 234 is provided with a coating 243 of pressure-sensitive adhesive which is protected by a release paper 237. When the adhesive patch 234 is heat-sealed to the attaching ring 231, the heat-sealable adhesive 240 bonds to the polyethylene attaching ring. If desired, the attaching ring 231 can be provided with a layer of hot melt adhesive, as previously described, which will fuse with the impregnated adhesive 240, thereby providing an even more secure attachment.

We have referred to the attachment between the polyethylene retainer ring and the polyethylene layer of the attaching ring as well as the attachment between the heat-sealable adhesive layer of the attaching ring and the fabric layer of the adhesive patch as "heat seal" bonds. However, these two attachments are different in character. The inner polyethylene to polyethylene attachment is a fusion bond which is obtained by melting and fusing the confronting thermoplastic surfaces. The outer attachment is both an adhesive and a mechanical bond, being obtained when the hot melt adhesive melts and flows into the pores of the fabric. Moreover, the bond between the polyethylene layer and the hot melt adhesive layer of the attaching ring in the preferred embodiment is obtained when the two layers are extruded together under heat, and this is a fusion or a chemical bond so that the two layers are essentially integrated.

In alternate embodiments where no gasket or retainer ring, such as ring 23, is provided around the pouch opening the attaching ring, such as ring 31, can be directly heat-sealed (fusion bonded) to the pouch, which will be formed of a heat-sealable material, such as polyethylene. Such embodiments will find use as wound drainage pouches, fecal collectors, enema bags, urostomy bags, etc. One such embodiment is illustrated in FIGS. 12 to 14 of the drawings, wherein the parts corresponding to those of FIGS. 1 to 6 have been given the same numbers except that the numbers have been primed.

Figure 12:
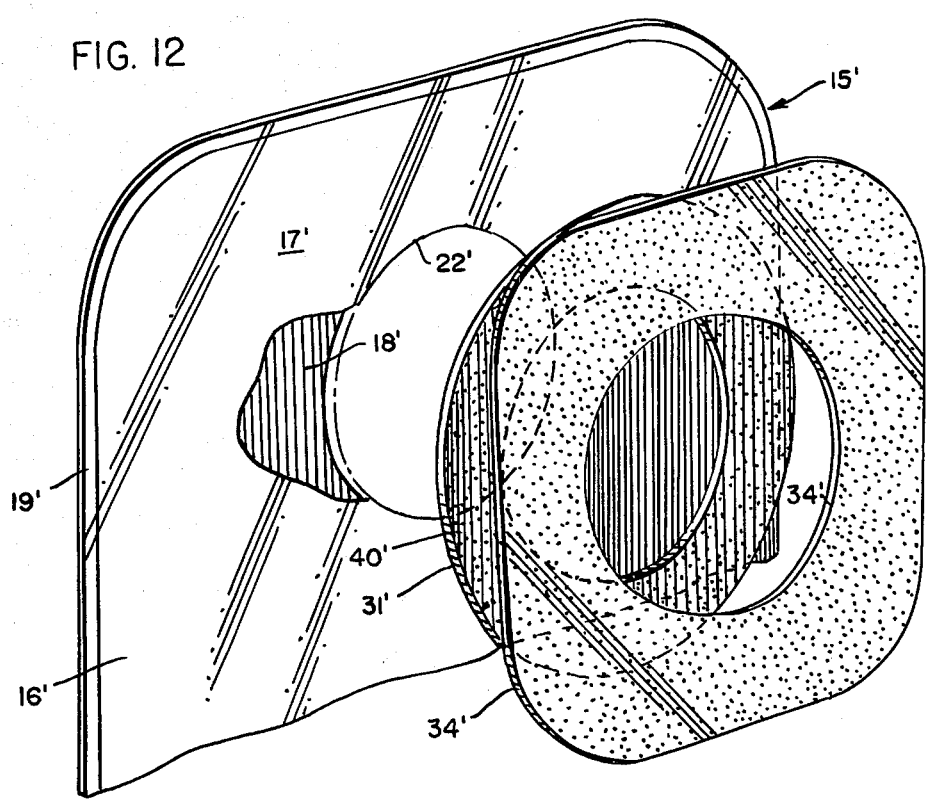
FIG. 12 is an exploded fragmentary perspective view of a modified drainage pouch of a modified construction in which the attaching ring is heat-sealed directly to the bag.
Figure 13:
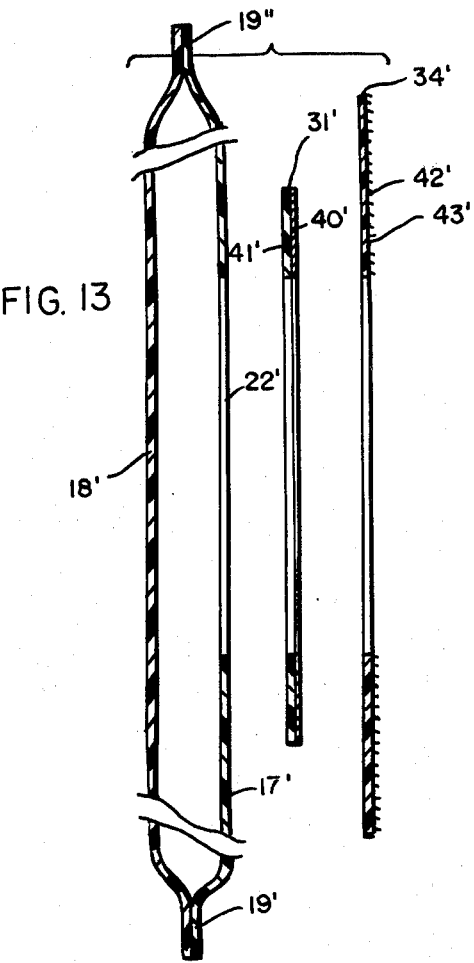
FIG. 13 is a vertical sectional view of the exploded pouch components of FIG. 12, upper and lower portions of the bag being shown broken away.
Figure 14:
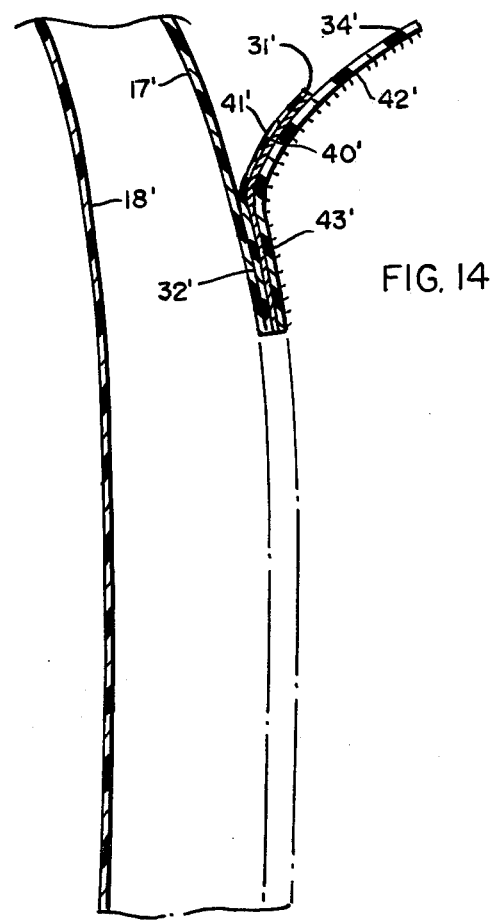
FIG. 14 is an enlarged detailed sectional view showing the components of the pouch of FIGS. 12 and 13 in assembled relation, the adhesive patch and attachment ring being flexed outwardly.

As shown in FIGS. 12 and 13, the inner side of attaching ring 31 prime is opposed to side 17 prime of bag 16 prime. There is no intervening retaining ring, as in the embodiment of FIGS. 1 to 6. The inner layer of attaching ring 31 prime is formed of thin, flexible thermoplastic sheet material, such as polyethylene, and the outer layer 40 prime is formed of a hot melt adhesive, as previously described. The bag sides 17 prime and 18 prime are formed of a thermoplastic sheet material such as polyethylene. In the assembly of the components, inner side 41 prime of the attaching ring is heat sealed in an annular area around bag opening 22 prime to bag wall 17 prime, as indicated at 32 prime in FIG. 14. The inner side of microporous adhesive patch 34 prime is heat-sealed fused to the outer side of attaching ring 31 prime by means of hot melt adhesive layer 40 prime, as previously described with respect to the prior embodiments. As shown more clearly in FIG. 14, the adhesive attachment of patch 34 prime to the outer side of ring 31 prime extends substantially across the full width of the ring, the outer attached portion extending beyond the heat sealed attachment 32 prime. In other words, the annular outer portion of the inner side of attaching ring 31 prime is unconnected to bag wall 17 prime and is thereby free to flex with patch 34 prime, as indicated in FIG. 14. As previously described, this provides a secure connection which minimizes the tendency of the microporous patch to tear while being worn.

Attaching ring 31 prime, being formed of nonporous plastic sheet material, effectively seals the portion of microporous adhesive patch 34 prime which is opposed thereto. Thus any fluids which tend to seep between the inner side of the microporous patch and the patient's body are prevented from passing through the microporous patch material unless the seepage extends to a point outwardly of the outer end of attaching ring 31 prime. Since this is unlikely to occur during normal use of the drainage pouch, an effective liquid barrier is provided by the construction while at the same time retaining the advantages of the breathable microporous adhesive patch which extends outwardly around attaching ring 31 prime.

We claim:

1. A sealing and attachment assembly for a drainage pouch having a moisture-impermeable bag formed of plastic sheet material with a drainage opening in one side thereof, the sealing and attachment assembly including an adhesive patch formed of microporous sheet material with an opening therein which is generally concentric with said opening in the bag, the patch having inner and outer sides and the outer side of the patch being coated with a pressure-sensitive adhesive for attachment to the body of a wearer, wherein the improvement comprises an annular attachment ring formed of flexible sheet material, said attaching ring having inner and outer sides and an opening which is generally concentric with the openings in the bag and in the patch, the inner side of the attaching ring being attached to the bag in a first area of attachment and the outer side of the attaching ring being attached to the inner side of the patch in a second area of attachment, the second area of attachment extending radially outwardly beyond the first area of attachment to provide an annular outer portion of the attaching ring which is unconnected to the bag and which is flexible and conformable by forces which are applied to the attaching ring and to the adhesive patch and which tend to remove the adhesive patch from the body so that said annular outer portion of the attaching ring and the portion of the adhesive patch attached thereto extends substantially linearly and the tendency of the adhesive patch to tear as a result of said forces is minimized, the outer periphery of the attaching ring being spaced inwardly of the outer periphery of the adhesive patch to provide a breathable outer portion of the adhesive patch which is uncovered by the attaching ring.

2. The structure of claim 1 in which the distance between the outer periphery of the attaching ring and the outer periphery of the adhesive patch is substantially greater than the width of the annular attaching ring whereby the area of said breathable, uncovered outer portion of the adhesive patch is substantially greater than the area of the attaching ring.

3. The structure of claim 1 in which said first and second areas of attachment extend annularly around the opening in the attaching ring.

4. The structure of claim 1 in which the attaching ring comprises an inner layer of plastic for providing a heat-sealed connection in said first area of attachment and an outer layer of adhesive which is attached to said adhesive patch in said second area of attachment.

5. The structure of claim 4 in which said adhesive is a hot melt adhesive.

6. The structure of claim 4 in which said adhesive is ethyl vinyl acetate.

7. The structure of claim 1 in which said adhesive patch is formed from a thin microporous non-woven fabric which is relatively easy to tear.

8. The structure of claim 1 in which said adhesive patch has a hot melt adhesive applied to the inner side thereof and the patch and the attaching ring are heat-sealed together in said second area of attachment.

9. The structure of claim 1 in which the outer side of the attaching ring is also secured to the inner side of the patch in an area which overlaps said first area of attachment.

10. A sealing and attachment assembly for a drainage pouch having a moisture-impermeable bag formed of plastic sheet material with a drainage opening in one side thereof, a retainer ring of relatively rigid plastic material having inner and outer sides and an opening which is generally concentric with the opening in the bag, the inner side of the retainer ring being attached to the bag around the bag opening, the improvement comprising an annular attaching ring formed of flexible sheet material, said attaching ring having inner and outer sides and an opening which is generally concentric with the opening in the bag and in the retainer ring, the inner side of the attaching ring being attached to the retainer ring in a first area of attachment, an adhesive patch formed of microporous sheet material with an opening therein which is generally concentric with the opening in the attaching ring, the patch having inner and outer sides and the outer side being coated with a pressure-sensitive adhesive for attachment to the body of a wearer, the outer side of the attaching ring being attached to the inner side of the patch in a second area of attachment, the second area of attachment extending radially outwardly beyond the first area of attachment to provide an annular outer portion of the attaching ring which is unconnected to the retainer ring and which is flexible and conformable by forces which are applied to the attaching ring and to the adhesive patch and which tend to remove the adhesive patch from the body so that said annular outer portion of the attaching ring and the portion of the adhesive patch attached thereto extends substantially linearly and the tendency of the adhesive patch to tear as a result of said forces is minimized, the outer periphery of the attaching ring being spaced inwardly of the outer periphery of the adhesive patch to provide a breathable outer portion of the adhesive patch which is uncovered by the attaching ring.

11. The structure of claim 10 in which the distance between the outer periphery of the attaching ring and the outer periphery of the adhesive patch is substantially greater than the width of the annular attaching ring whereby the area of said breathable, uncovered outer portion of the adhesive patch is substantially greater than the area of the attaching ring.

12. The structure of claim 10 in which said first and second areas of attachment extend annularly around the opening in the attaching ring.

13. The structure of claim 10 in which the attaching ring comprises an inner layer of plastic for providing a heat-sealed connection in said first area of attachment and an outer layer of adhesive which is attached to said adhesive patch in said second area of attachment.

14. The structure of claim 13 in which said adhesive is a hot melt adhesive.

15. The structure of claim 13 in which said adhesive is ethyl vinyl acetate.

16. The structure of claim 10 in which said adhesive patch is formed from a thin microporous non-woven fabric which is relatively easy to tear.

17. The structure of claim 10 in which said adhesive patch has a hot melt adhesive applied to the inner side thereof, the patch and the attaching ring being heat-sealed together in said second area of attachment.

18. The structure of claim 10 in which the outer side of the attaching ring is also secured to the inner side of the patch in an area which overlaps said first area of attachment.

19. A sealing assembly for a drainage pouch, the drainage pouch including a moisture-impermeable bag having a drainage opening and an annular plastic retainer ring secured to the bag around the drainage opening, the sealing assembly comprising an annular layer of flexible plastic which is fused to the plastic retainer ring in a first area of attachment, an adhesive patch formed of microporous non-woven fabric having pressure-sensitive adhesive applied to one side thereof and having an opening therein which is generally concentric with the opening in the attaching ring, the retainer, and the bag, and a layer of hot melt adhesive between said layer of plastic and the side of the non-woven fabric opposite the pressure-sensitive adhesive, the hot melt adhesive being bonded to the layer of plastic and mechanically bonded to the non-woven fabric in a second area of attachment which extends radially outwardly of the first area of attachment to provide a portion of the layer of plastic which is unconnected to the retainer ring, and which is flexible and conformable by forces which tend to remove the adhesive patch from the body so that said portion of the layer of plastic and the portion of the adhesive patch attached thereto extend substantially linearly and the tendency of the adhesive patch to tear as a result of said forces is minimized, the outer periphery of said annular layer of flexible plastic being spaced inwardly of the outer periphery of the adhesive patch to provide a breathable outer portion of the adhesive patch which is uncovered by said annular layer.

20. The structure of claim 19 in which the distance between the outer periphery of said annular layer of flexible plastic and the outer periphery of the adhesive patch is substantially greater than the width of said annular layer of flexible plastic whereby the area of said breathable, uncovered outer portion of the adhesive patch is substantially greater than the area of the attaching ring.

21. A sealing assembly for a drainage pouch, the drainage pouch including a moisture-impermeable bag having a drainage opening, the sealing assembly comprising an annular attaching ring formed of flexible sheet material secured to said bag by a first area of attachment extending around the bag opening, and an adhesive patch formed of microporous sheet material, the adhesive patch having an opening therein which is generally concentric with the openings in the attaching ring and the bag, the adhesive patch being secured to the attaching ring by a second area of attachment extending around the attaching ring by and extending radially outwardly beyond said first area of attachment, the adhesive patch being adapted to be adhesively secured to the body of a patient around a drainage opening, the portion of the flexible attaching ring which extends radially outwardly beyond the first area of attachment of the attaching ring to the bag being flexible and conformable by forces which are applied to the attaching ring and to the adhesive patch which tend to remove the adhesive patch from the body so that said radially outwardly extending portion of the attaching ring and the portion of the adhesive patch attached thereto extend substantially linearly and the tendency of the adhesive patch to tear as a result of said forces is minimized, the outer periphery of the attaching ring being spaced inwardly of the outer periphery of the adhesive patch to provide a breathable outer portion of the adhesive patch which is uncovered by the attaching ring.

22. The structure of claim 21 in which the distance between the outer periphery of the attaching ring and the outer periphery of the adhesive patch is substantially greater than the width of the annular attaching ring whereby the area of said breathable, uncovered outer portion of the adhesive patch is substantially greater than the area of the attaching ring.

23. The structure of claim 21 in which said second area of attachment extends substantially across the annular width of said attaching ring.

24. A sealing assembly for a drainage pouch, the drainage pouch including a moisture-impermeable bag having a drainage opening and an annular retainer ring secured to the bag around the drainage opening, the sealing assembly comprising an annular attaching ring formed of flexible sheet material secured to the retainer ring by a first area of attachment extending around the attaching ring, and an adhesive patch formed of microporous sheet material, the adhesive patch having an opening therein which is generally concentric with the openings in the attaching ring, the retainer, and the bag, the adhesive patch being secured to the attaching ring by a second area of attachment which extends around the attaching ring by a second area of attachment which extends around the attaching ring and which extends radially outwardly beyond the first area of attachment, the adhesive patch around a drainage opening, the portion of the flexible attaching ring which extends radially outwardly beyond the first area of attachment of the attaching ring to the retainer ring being flexible and conformable by forces which are applied to the attaching ring and to the adhesive patch and which tend to remove the adhesive patch from the body so that the portions of the attaching ring and the adhesive patch adjacent the attachment therebetween extend substantially linearly and the tendency of the adhesive patch to tear as a result of said forces is minimized, the outer periphery of the attaching ring being spaced inwardly of the outer periphery of the adhesive patch to provide a breathable outer portion of the adhesive patch which is uncovered by the attaching ring.

25. The structure of claim 24 in which the distance between the outer periphery of the attaching ring and the outer periphery of the adhesive patch is substantially greater than the width of the annular attaching ring whereby the area of said breathable, uncovered outer portion of the adhesive patch is substantially greater than the area of the attaching ring.

* * * * *

UNITED STATES PATENT AND TRADEMARK OFFICE
CERTIFICATE OF CORRECTION

PATENT NO. : 4,213,458

DATED : July 22, 1980

INVENTOR(S) : Nolan, John L., and Nordby, Harvey M.

It is certified that error appears in the above-identified patent and that said Letters Patent is hereby corrected as shown below:

Column 12, lines 19-20, cancel "by a second area of attachment which extends around the attaching ring".

Column 12, line 23, after "patch" should be added -- being adapted to be adhesively secured to the body of a patient --.

Signed and Sealed this

Twenty-seventh Day of January, 1987

Attest:

DONALD J. QUIGG

Attesting Officer    Commissioner of Patents and Trademarks